United States Patent [19]

Gorman, Jr. et al.

[11] Patent Number: 5,569,206
[45] Date of Patent: Oct. 29, 1996

[54] TROCAR ADAPTER SEAL

[75] Inventors: Charles E. Gorman, Jr., Hamden, Conn.; Michael Ciccolella, Lake Carmel, N.Y.; Robert C. Smith, Watertown, Conn.; Thomas D. Guy, Fairfield, Conn.; Kurt Azarbarzin, Ridgefield, Conn.

[73] Assignee: United States Surgical Corporation, Norwalk, Conn.

[21] Appl. No.: 335,517

[22] Filed: Nov. 7, 1994

Related U.S. Application Data

[63] Continuation of Ser. No. 121,017, Sep. 14, 1993, abandoned.

[51] Int. Cl.$^6$ ..................................................... A61M 5/178
[52] U.S. Cl. ..................................................... 604/167
[58] Field of Search .................................... 604/167, 256

[56] References Cited

U.S. PATENT DOCUMENTS

| | | |
|---|---|---|
| 3,994,287 | 11/1976 | Turp et al. . |
| 4,000,739 | 1/1977 | Stevens . |
| 4,177,814 | 12/1979 | Knepshield et al. . |
| 4,231,400 | 11/1980 | Friedling et al. . |
| 4,392,485 | 7/1983 | Hiltebrandt . |
| 4,601,710 | 7/1986 | Moll . |
| 4,634,421 | 1/1987 | Hegemann . |
| 4,654,030 | 3/1987 | Moll et al. . |
| 4,673,393 | 6/1987 | Suzuki et al. . |
| 4,705,511 | 11/1987 | Kocak . |
| 4,715,360 | 12/1987 | Akui et al. ................................ 604/256 |
| 4,909,798 | 3/1990 | Fleischhacker ......................... 604/256 |
| 4,929,235 | 5/1990 | Merry et al. . |
| 4,944,732 | 7/1990 | Russo ...................................... 604/256 |
| 4,960,412 | 10/1990 | Fink . |
| 5,080,654 | 1/1992 | Picha et al. ............................. 604/167 |
| 5,104,383 | 4/1992 | Shichman ................................ 604/256 |
| 5,127,909 | 7/1992 | Shichman . |
| 5,211,633 | 5/1993 | Stouder, Jr. ............................. 604/167 |
| 5,221,264 | 6/1993 | Wilk et al. .............................. 604/167 |
| 5,242,389 | 9/1993 | Schrader et al. ....................... 604/167 |
| 5,263,944 | 11/1993 | Vidal et al. ............................. 604/256 |
| 5,300,036 | 4/1994 | Mueller et al. . |
| 5,312,362 | 5/1994 | Pfolsgraf et al. ...................... 604/167 |
| 5,338,307 | 8/1994 | Stephens et al. . |
| 5,407,433 | 4/1995 | Loomas ................................... 604/256 |
| 5,437,646 | 8/1995 | Hunt et al. ............................. 604/167 |

FOREIGN PATENT DOCUMENTS

| | | |
|---|---|---|
| 0051718 | 5/1982 | European Pat. Off. . |
| 0113520 | 7/1984 | European Pat. Off. . |
| 0521590 | 1/1993 | European Pat. Off. . |
| 7527593 | 4/1976 | France . |
| 7145806 | 6/1972 | Germany . |
| 3042229 | 5/1982 | Germany . |
| 1482857 | 8/1977 | United Kingdom . |
| 2019219 | 10/1979 | United Kingdom . |
| 92014499 | 9/1992 | WIPO ..................................... 604/264 |
| 9304717 | 3/1993 | WIPO . |

OTHER PUBLICATIONS

Information Booklet for Auto Suture® Surgiport® Disposable Surgical Trocar and Sleeve 1988.
Richard Wolf Product Catalog, p. I–86.
Information Booklet for Endo Path Surgical Trocar Universal Reducer @ 1992 Ethicon, Inc.

*Primary Examiner*—Todd E. Manahan

[57] ABSTRACT

An adapter seal is provided which is adapted to be mounted to a cannula assembly. The adapter seal preferably defines a channel which is adapted to cooperate with walls extending upward from a cannula housing. In a second embodiment, a button is provided that may be repositioned such that its aperture aligns with an aperture formed in the body member of the adapter seal. The button is preferably joined to the body member by a flexible strap.

3 Claims, 9 Drawing Sheets

TROCAR ADAPTER SEAL

This is a continuation of application Ser. No. 08/121,017, filed on Sep. 14, 1993, abandoned.

BACKGROUND OF THE INVENTION

1. Technical Field

The present invention relates to an adapter seal for use with a cannula assembly of a trocar and to a method for performing surgical procedures using the adapter seal.

2. Description of the Prior Art

Endoscopic and laparoscopic surgical procedures are often performed with an insufflatory gas present within the body cavity being accessed to provide an operative field for the surgeon. Insufflatory surgery is generally performed by puncturing the body wall in the region of the desired body cavity with a pneumoperitoneum needle, e.g., a Verres needle. The needle includes a hollow stylet through which insufflatory gas may be introduced to the body cavity.

A trocar assembly may then be used to provide a port of entry into the body cavity for introduction of endoscopic surgical instruments, e.g., graspers, dissectors, scopes, clip appliers, stapling devices, and the like. These instruments have differing sizes, for example, some instruments have a cross-sectional diameter in their elongate sections on the order of 5 mm whereas others have a diameter of 10 mm or larger. The trocar assembly for creating the port of entry includes an obturator assembly which generally includes a piercing tip at the distal end of an obturator and an obturator housing, and a cannula assembly which generally includes a tubular cannula or sleeve and a cannula housing. The obturator is adapted to be inserted through the cannula such that the piercing tip is exposed from the cannula at the distal end thereof. In this operative condition, the trocar housing and cannula housing generally assume a mating relationship.

In recognition of the variability in instrument diameters, cannulas are available with different inner diameters. Commercially available trocar assemblies offer cannulas having a broad range of inner diameters, ranging from 3 to 15 mms (e.g., 3, 5, 7, 8, 10, 11, 12 and 15 mm sizes). After the body wall is penetrated by the piercing tip, the obturator assembly is generally separated from the cannula assembly, leaving the cannula extending into the body cavity for receipt of surgical instrumentation, as described above.

In order to maintain the insufflatory gas within the body cavity, thereby maintaining the surgeon's operative field, a cannula housing is generally provided with a seal system that is designed to provide a substantial fluid-tight seal in the absence of a surgical instrument positioned therethrough, and to sealingly engage a surgical instrument inserted therethrough. Thus, for example, a trocar assembly which is nominally designated a "10 mm trocar" would generally include a cannula having an internal diameter sufficiently greater than 10 mm to accommodate 10 mm instruments, and a cannula housing that included a seal system adapted to provide a fluid-tight seal in the absence of a surgical instrument and to sealingly engage instruments of 10 mm diameter. More recently, cannula housings have been provided with seal systems that are designed to sealingly engage surgical instrumentation across a range of instrument diameters, e.g., 10 to 12 mm, 4 to 5 mm, etc. Such flexibility is desirable because, with the advent and increased acceptance of additional minimally invasive surgical procedures, surgeons desire to utilize instruments of varying diameters in surgical procedures while maintaining the number of cannula assemblies to a minimum.

U.S. Pat. Nos. 4,601,710 to Moll and 4,654,030 to Moll et al. disclose trocar assemblies which include an elongate trocar obturator having a piercing tip at its front end and an elongate trocar tube or cannula in which the trocar obturator is housed. As shown in the '030 patent, a flapper valve may be employed to close off the cannula passage after the trocar obturator or other instrument has been withdrawn.

A gasket may also be employed to ensure a seal between the trocar assembly and an instrument inserted therein. U.S. Pat. No. 4,000,739 to Stevens, for example, teaches a hemostasis cannula having a pair of juxtaposed gaskets mounted in the passageway to the cannula, the first having a round hole and the second a Y-shaped slit. U.S. Pat. No. 3,994,287 to Turp et al. describes a trocar assembly which includes a flexible insulating ting received in a flange and a collar which retains the flexible ring in the flange. The flexible ting is allowed to flex as an instrument is inserted into the cannula and provides a seal with the instrument to prevent gas leakage. U.S. Pat. No. 4,112,932 to Chiulli describes a cannula which includes a turret member having first and second apertures. The turret member is movable such that a selected aperture is aligned with the bore of the cannula for passage of an instrument.

Trocar adapters and reducer sleeves which are adapted to be used in conjunction with a cannula assembly have also been provided for reducing or varying the size of the aperture for receipt of surgical instrumentation. U.S. Pat. No. 5,104,383 to Shichman describes an adapter seal which is adapted to be detachably associated with a cannula assembly to reduce the diameter of the aperture therethrough. The adapter seal is preferably provided with a stabilizer plate to limit the eccentric movement of an instrument relative to the seal.

Despite the availability of trocar assemblies having cannulas of various sizes and the availability of adapter seals and reducer sleeves for use in conjunction therewith, there remains a need for apparatus that may be used to vary the size of the aperture within a cannula assembly in a more efficient and efficacious manner.

SUMMARY OF THE INVENTION

It is an object of the present invention to provide an adapter seal for use with a cannula assembly which permits the use of variously sized instruments with the cannula assembly.

It is another object of the present invention to provide an adapter seal which may be securely and conveniently received by the cannula assembly.

It is a further object to provide an adapter seal which provides an effective seal with an endoscopic surgical instrument.

It is yet another object of the invention to provide a method whereby surgical instruments of differing sizes may be used endoscopically through a single cannula.

These and other objects of the invention are realized by an adapter seal which comprises an adapter body formed of an elastomeric material which defines a rim extending around its periphery that is adapted to sealingly engage a correspondingly configured cannula housing. In a preferred embodiment, the adapter body is fabricated from a rubber, such as natural rubber or santoprene, and defines a substantially rectangular peripheral rim. A transverse lip or tab may be formed on the adapter body to facilitate manipulation of the adapter seal, e.g., placement on and removal from a cannula housing. A channel which extends around the perimeter of the adapter body is advantageously defined within the peripheral rim and is adapted to receive proximally extending faces on the cannula housing.

The adapter body includes an aperture of predetermined diameter which is adapted to allow passage of a surgical instrument therethrough. The adapter body sealingly engages surgical instrumentation of corresponding diameter passed through the aperture formed therein. The adapter body may be of reduced thickness in the region surrounding the adapter body aperture to provide additional resilience thereto. A stabilizer plate of relatively rigid material may also be provided, the stabilizer plate being adapted to be received within a recessed region on the proximal side of the adapter body. The stabilizer plate generally has an aperture of larger diameter than the aperture formed in the adapter body. The stabilizer plate cooperates with the adapter body to provide rigidity thereto. The aperture in the stabilizer plate is sized to cooperate with and restrict excessive eccentric motion of an instrument passed therethrough relative to the adapter body which could break the gas seal formed therebetween.

In one embodiment of the invention, an elastomeric strap is associated with the adapter body. At one end of the elastomeric strap a resilient gasket is provided which includes an aperture formed therethrough. The strap is configured and dimensioned to permit alignment of the gasket aperture with the adapter body aperture and, if applicable, the stabilizer plate aperture. The gasket aperture is preferably of reduced diameter relative to the diameter of the adapter body aperture, thereby allowing instrumentation of smaller diameter, i.e., of diameters corresponding to the diameter of the gasket aperture, to be introduced through the cannula assembly without loss of pneumoperitoneum gas.

In a further embodiment of the invention, the gasket comprises a substantially cylindrical gasket body having a circumferential bead on an exterior face thereof. The stabilizer plate optionally forms a corresponding, proximally-directed, cylindrical cavity which is adapted to sealingly receive the cylindrical gasket body. A flange may be provided at the proximal end of the cylindrical gasket body to define an abutment face which engages the stabilizer plate when the cylindrical gasket body is fully seated within the corresponding cylindrical cavity. An elastomeric tab optionally extends from the cylindrical gasket body, e.g., at the side opposite the point at which the strap is associated therewith, to facilitate separation of the gasket from the stabilizer plate/adapter body.

In use, a cannula, e.g., a 10 mm cannula, may inserted into a body cavity in a conventional manner, and the sharp-tipped trocar removed therefrom. At this point, the surgeon is only in a position to endoscopically employ instruments having an elongate portion having an outer diameter of about 10 mm without the loss of pneumoperitoneum gas. Should the surgeon desire to insert an instrument of smaller diameter, e.g., a 5 mm instrument, the adapter seal of the present invention is positioned such that the elongate portion of the 5 mm instrument may be inserted through the aperture in the adapter body and through the 10 mm cannula. The adapter body cooperates with the cannula assembly through interaction between the peripheral rim and peripheral channel of the adapter body cooperating with corresponding proximally extending faces on the cannula housing. The aperture through the adapter body sealingly engages 5 mm instruments inserted therethrough. The surgeon may subsequently use larger or smaller diameter instruments by removing the 5 mm adapter body from the cannula housing and positioning a second adapter body of different aperture size thereon, or by using the 10 mm cannula with a 10 mm instrument.

Alternatively, the surgeon may mount an adapter body of the present invention on a cannula assembly, the adapter body including a strap to which is joined a gasket having an aperture of lesser diameter than the aperture formed in the adapter body. When it is desired to introduce instrumentation of lesser diameter through the cannula assembly without losing pneumoperitoneum gas, the gasket may be positioned relative to the adapter body such that their respective apertures align. Preferably, the gasket is seated within a cavity formed by the stabilizer plate to stabilize the gasket relative to the cannula assembly. Thereafter, larger diameter instruments may be utilized by removing the gasket The adapter body may also be removed from the cannula housing, as discussed above, and instruments may be utilized through the cannula assembly based on the seal system provided therewith.

The present invention thus provides the surgeon with tremendous flexibility in the selection and use of surgical instruments in endoscopic procedures without the loss of pneumoperitoneum gas.

BRIEF DESCRIPTION OF THE DRAWINGS

The present invention will become more apparent from the following detailed description taken in conjunction with the accompanying drawings in which:

FIG. 2A is a sectional side view of the adapter body of FIG. 1 taken along line 2—2 including beads formed on the interior face of the interior walls;

FIG. 6A is a perspective view of an alternative embodiment of the adapter seal of the present invention having a plurality of straps and buttons with apertures of varying diameter;

FIG. 8A is a side view, partially in cross-section, of the alternate embodiment of FIG. 6 including a hinge;

DETAILED DESCRIPTION OF THE INVENTION

Figure 1:
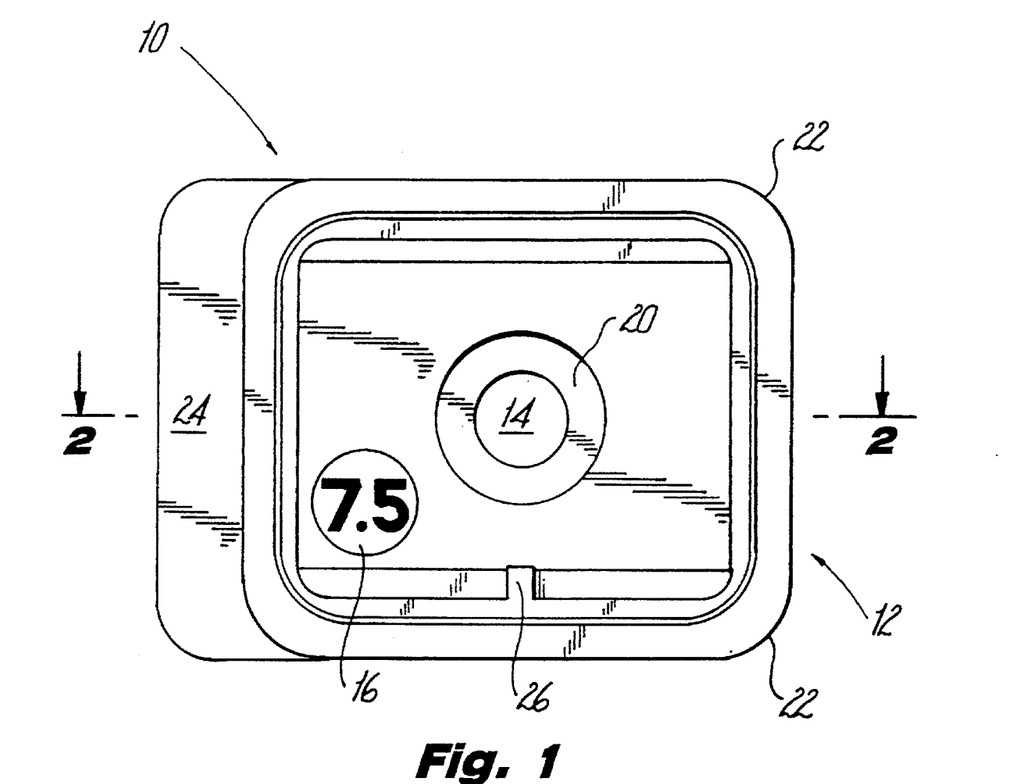
FIG. 1 is a bottom view of an adapter body of the present invention.
Figure 2:
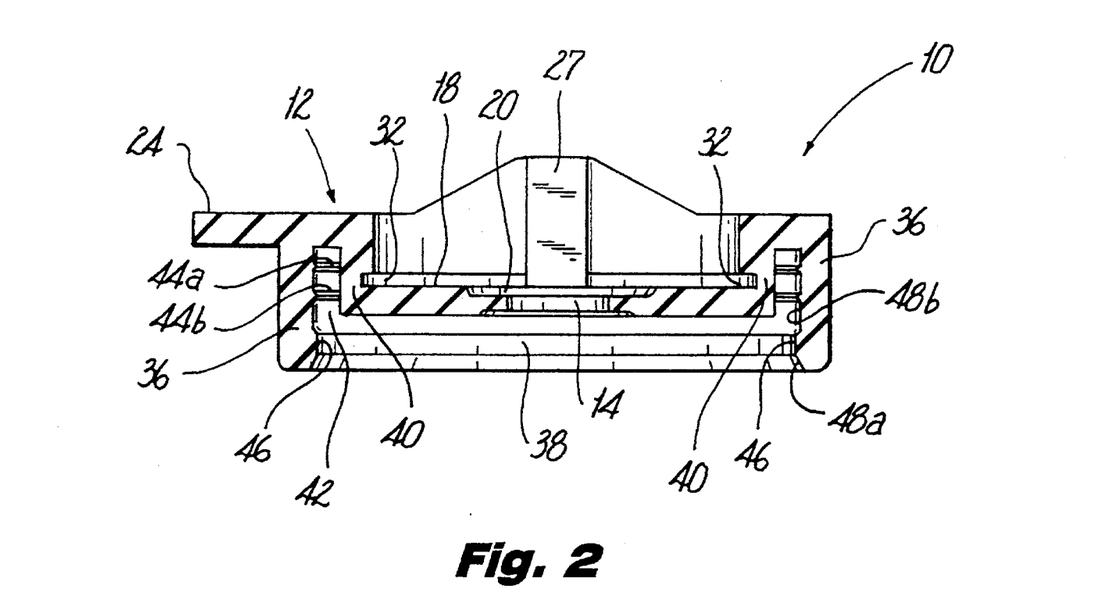
FIG. 2 is a sectional side view of the adapter body of FIG. 1 taken along line 2—2.

Referring initially to FIGS. 1 and 2 of the invention, adapter seal 10 includes an adapter body 12 which defines an aperture 14. The size of aperture 14 is selected to sealingly engage instruments of a predetermined diameter. In the adapter seal shown in FIG. 1, aperture 14 is of a diameter of about 7 mm and is designed to sealingly engage instruments ranging in diameter from 7 to 8 mm. A size indicia 16 is printed or molded into transverse face 18 of adapter body 12 to alert the surgeon as to the aperture diameter. In this case, the indicia is "7.5" which indicates to the surgeon that instruments of 7 to 8 mm may be used therethrough. Transverse face 18 is of reduced thickness in central region 20 surrounding aperture 14, thereby increasing the resilience and flexibility thereof and facilitating the introduction and removal of instrumentation in sealing engagement therewith.

Figure 5A:
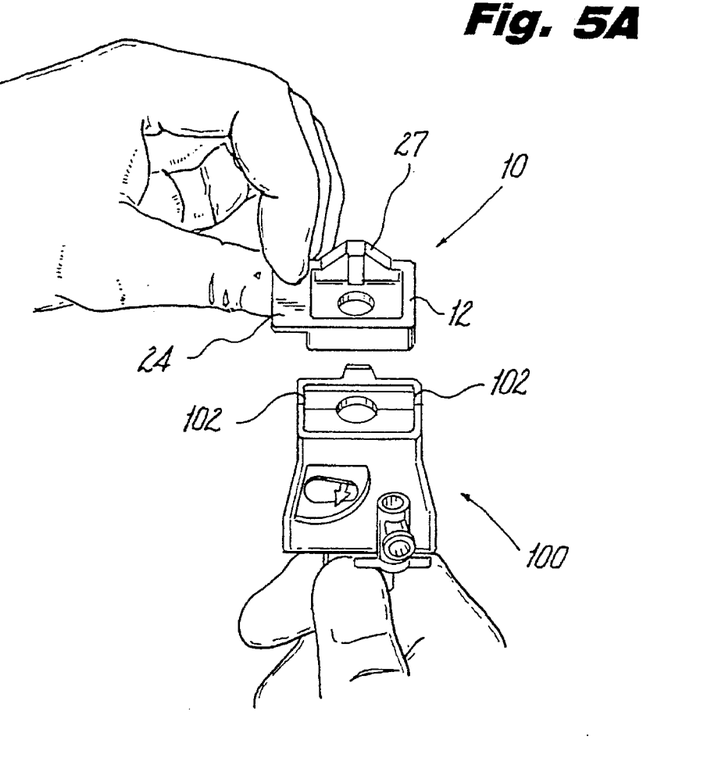
FIGS. 5A and 5B are schematic views of an adapter seal of the present invention being mounted to a cannula housing.
Figure 5B:
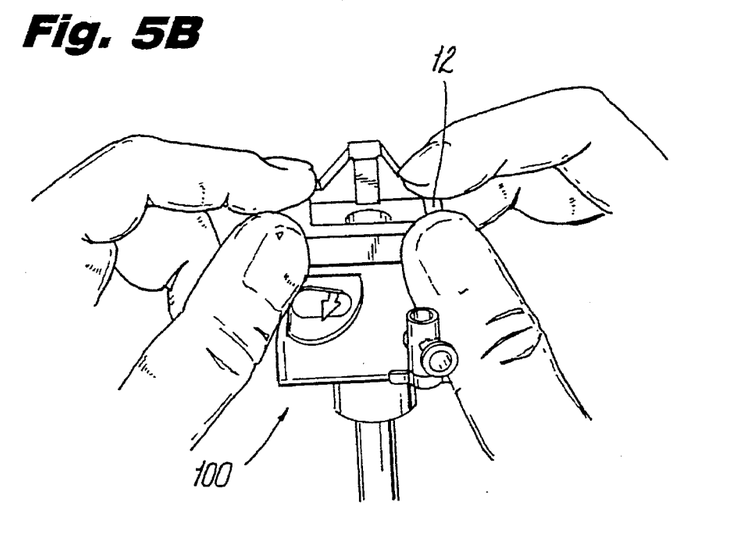

Adapter body 12 is of substantially rectangular configuration with rounded corners 22. The shape of adapter body 12 corresponds to the shape of the Surgiport* cannula housing 100 which is marketed by United States Surgical Corporation, Norwalk, Conn. and shown in FIG. 5 hereto. Lip 24 is formed on adapter body 12 to facilitate placement and removal of adapter seal 10 from cannula housing 100. In addition, an alignment notch 26 and a trapezoidal projection 27 are formed in adapter body 12 to facilitate cooperation with corresponding structures on the Surgiport* cannula housing 100. As will be readily apparent to one of ordinary skill in the art, however, adapter body 12 may be fabricated in a variety of shapes and sizes to facilitate its use with other cannula assemblies, e.g., cannula assemblies marketed by other manufacturers, without departing from the teachings of the present invention.

Adapter body 12 is fabricated from an elastomeric material, e.g., santoprene or natural rubber, to provide a desired degree of resilience and flexibility thereto. This resilience and flexibility are desirable to allow efficient interaction between adapter seal 10 and a cannula assembly, and to facilitate sealing engagement with an instrument passed through aperture 14. Adapter body 12 is adapted to receive a stabilizer plate 28 (see FIGS. 3 and 4) which is made of substantially rigid material, e.g., an ABS polymer resin. Stabilizer plate 28 improves the reliability of the seal provided by adapter seal 10 in conjunction with a surgical instrument inserted through aperture 14. The flexibility and resilience of adapter body 12 allows the surgeon to manipulate instrumentation at extreme angles relative to adapter seal 10, thereby jeopardizing the seal between adapter seal 10 and the instrument. Stabilizer plate 28, and particularly the perimeter 29 of orifice 30 formed therein, restricts the freedom of movement of the instrument relative to the adapter seal 10, thereby ensuring a seal will be maintained between the instrument and adapter body 12. Stabilizer plate 28 may be provided with a region of increased cross-section 31 surrounding orifice 30 to enhance the ability of stabilizer plate 28 to maintain the seal between adapter body 12 and an instrument inserted therethrough.

Figure 3:
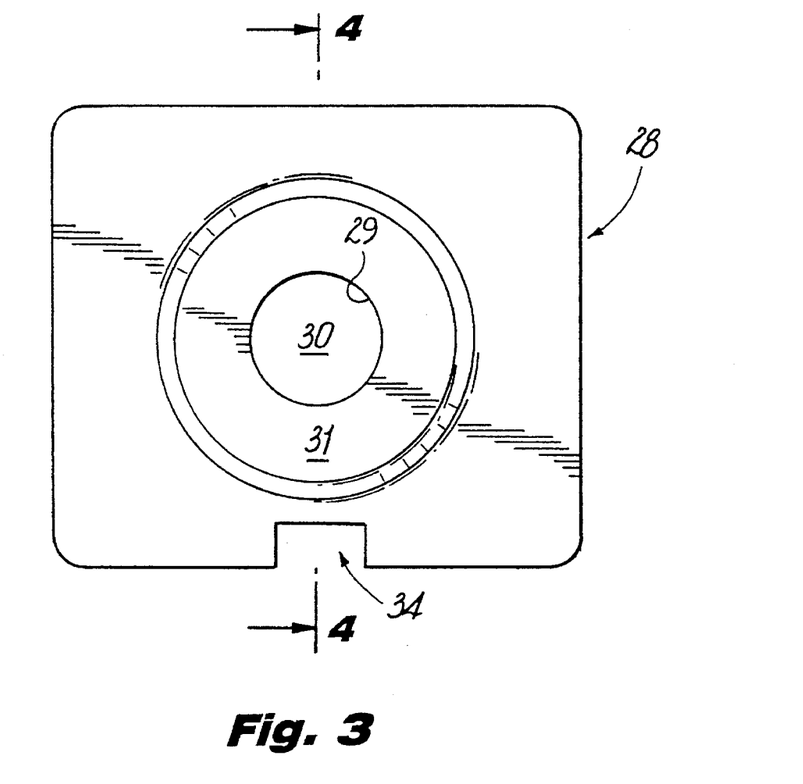
FIG. 3 is a bottom view of a stabilizer plate according to the present invention.
Figure 4:
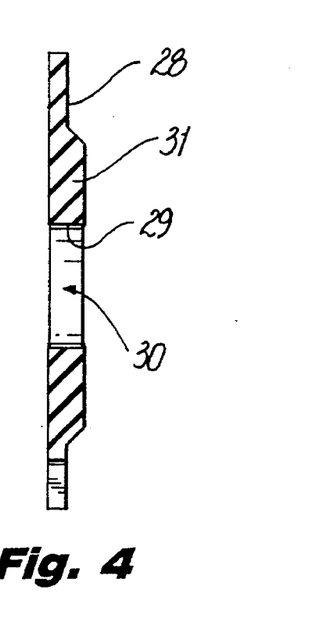
FIG. 4 is a sectional side view of the stabilizer plate of FIG. 3 taken along line 4—4.

Stabilizer plate 28 is adapted to fit snugly within a peripheral notch 32 formed in adapter body 12. When fitted therewithin, stabilizer plate 28 lies in substantial coplanar alignment with transverse face 18 of adapter body 12. A cutout 34 is provided in one side of stabilizer plate 28 to cooperate with alignment notch 26 of adapter body 12. Preferably, size indicia are printed on the face of stabilizer plate 28 which is proximally directed when stabilizer plate 28 is positioned in peripheral notch 32 to further alert the surgeon to the instruments which adapter seal 10 is designed to accommodate.

Adapter body 12 includes side walls 36 which define a peripheral rim of adapter body 12 and an interior region 38, and interior walls 40 which, in conjunction with side walls 36, define a channel 42 which extends around the perimeter of adapter body 12. A pair of inwardly directed beads 44a and 44b and a lip 46 are formed on the interior face of side walls 36. Alternatively, beads 44a and 44b and lip 46 may be formed on the interior face of interior walls 40 (FIG. 2A). Channel 42 is adapted to receive proximally extending faces 102 on cannula housing 100 (see FIG. 5). Beads 44a, 44b and lip 46 provide increased frictional engagement between adapter seal 10 and cannula housing 100, thereby increasing the force required to separate one from the other. Beads 44a, 44b and lip 46 are preferably provided with tapered faces, e.g., tapered faces 48a and 48b adjacent lip 46, thereby facilitating positioning of adapter seal 10 on cannula assembly 100. The resilience and flexibility of adapter body 12 and the presence of tapered faces, e.g., tapered faces 48a, 48b, facilitate separation of adapter seal 10 from cannula housing 100 when the surgeon so desires.

In use, a surgeon places a cannula assembly through a body wall in a conventional manner such that a port of entry for surgical instrumentation is provided. The surgeon may utilize instrumentation sized to cooperate with the selected cannula assembly, and particularly the seal assembly of the selected cannula assembly, without loss of pneumoperitoneum gas. If the surgeon desires to use instruments of smaller diameter than the cannula assembly's seal assembly is designed to accommodate, an adapter seal 10 of the present invention may be mounted to the cannula assembly as shown in FIGS. 5A and 5B. The surgeon aligns channel 42 with the proximal extending faces 102 on the cannula housing 100. Adapter seal 10 is firmly mounted on the cannula housing by pressing downward on adapter body 12 such that beads 44a, 44b and lip 46 engage the faces 102 of the cannula housing 100. A seal is thus formed between the cannula housing 100 and adapter seal 10.

The surgeon proceeds with the surgical procedure by inserting surgical instrument(s) through aperture 14 in adapter body 12. Adapter body 12 thus sealingly engages the surgical instrument, thereby providing a gas seal therebetween. Stabilizer plate 28 restricts the freedom of movement of the instrument relative to the adapter seal 10, thereby ensuring a seal will be maintained between the instrument and adapter body 12. As the surgical procedure continues, if the surgeon desires to use a different sized instrument through cannula assembly 100, a different adapter seal 10 having a different size aperture 14 may be placed on the cannula housing 100 or the cannula assembly 100 may be utilized without an adapter seal 10, i.e., with only the seal assembly present in the cannula housing 100.

Figure 6:
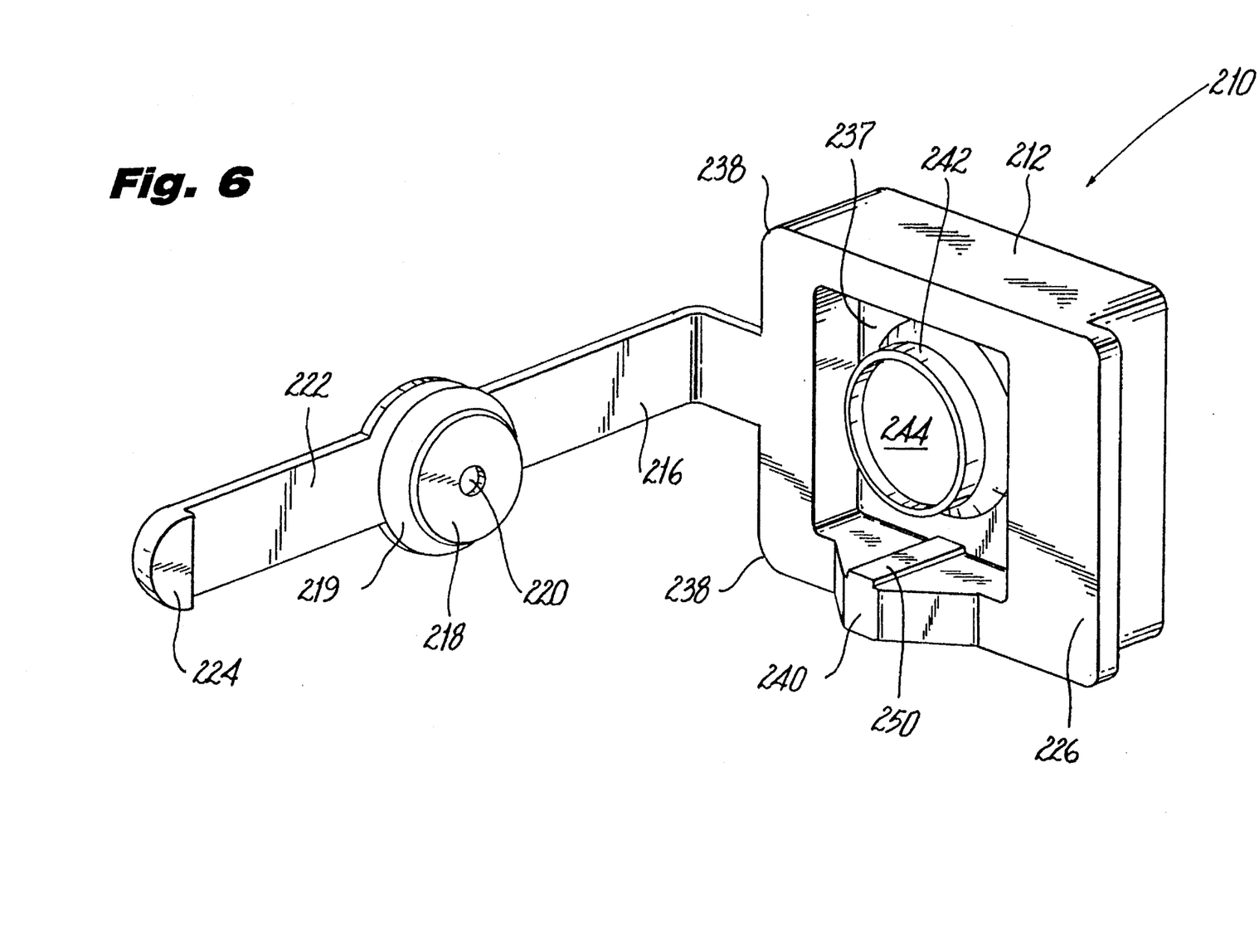
FIG. 6 is a perspective view of an alternative embodiment of the adapter seal of the present invention.
Figure 7:
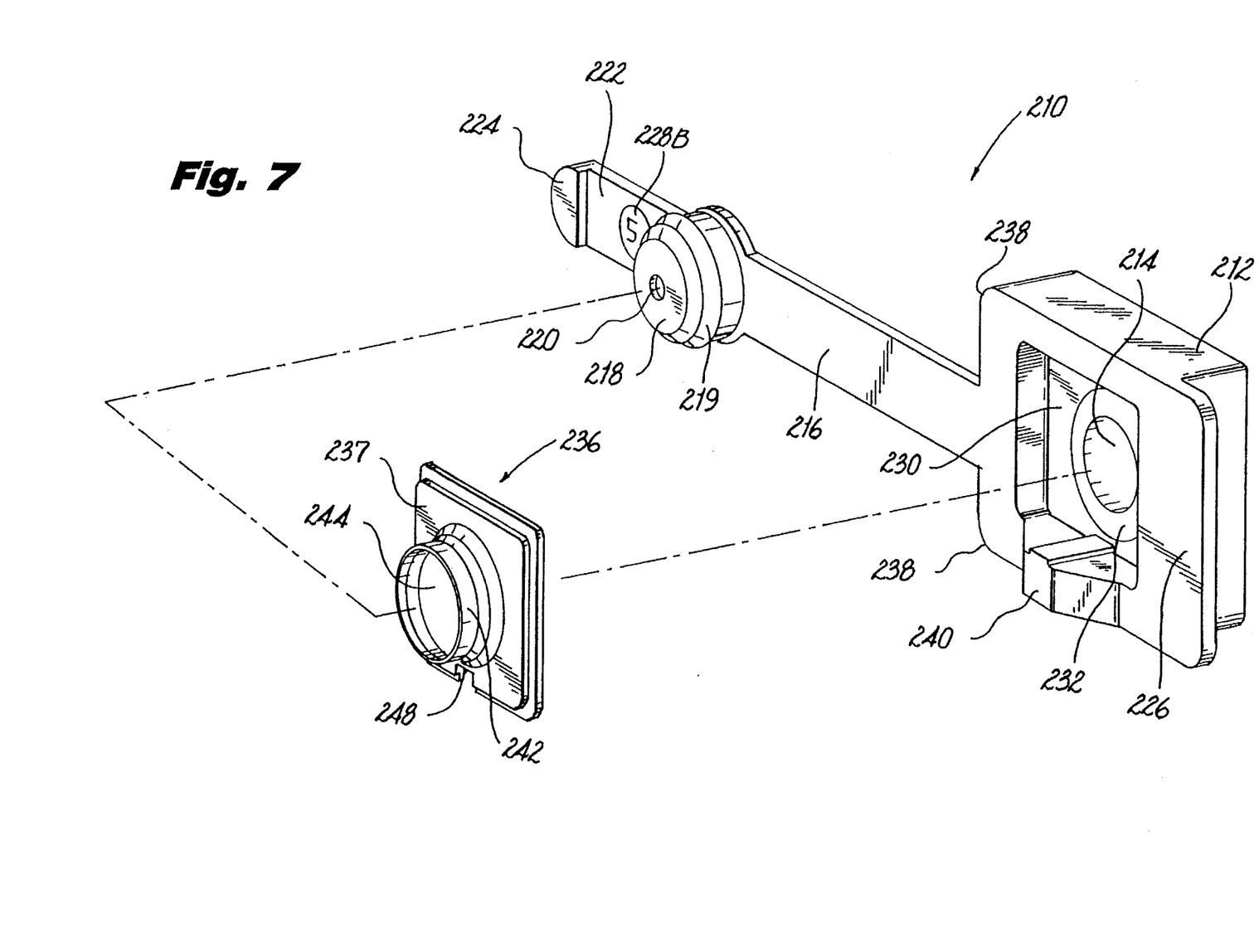
FIG. 7 is a perspective view of the alternate embodiment of FIG. 6 with pans separated.
Figure 8:
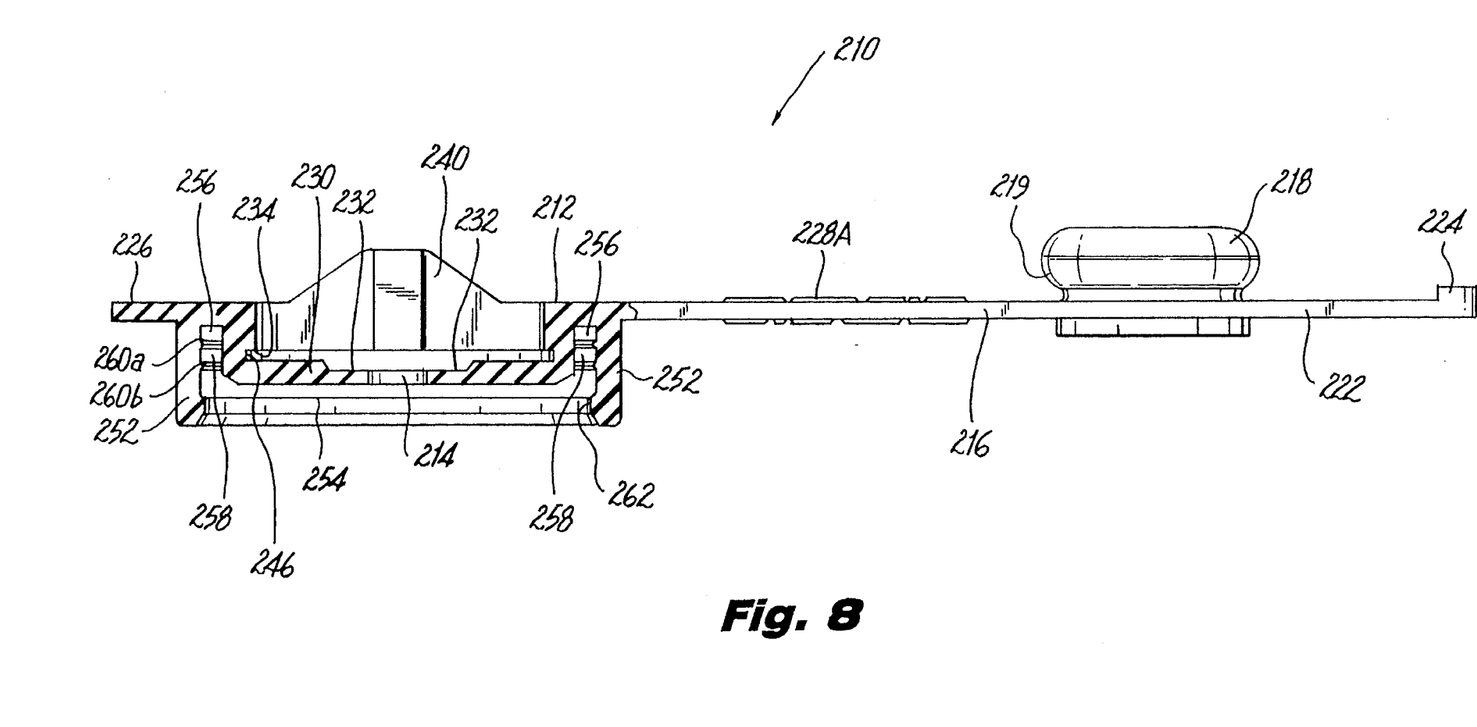
FIG. 8 is a side view, partially in cross-section, of the alternate embodiment of FIGS. 6.

In an alternate embodiment of the invention and with reference to FIGS. 6 to 8, adapter seal 210 includes an adapter body 212 which defines an aperture 214. Adapter seal 210 also includes a strap 216 which extends from a side of adapter body 212. A button 218 is positioned on strap 216 and includes a button aperture 220 of reduced diameter relative to aperture 214. The sizes of apertures 214 and 220 are selected to sealingly engage instruments of predetermined diameters. A size indicia may be printed or molded onto adapter body 212 at an appropriate location(s), e.g., molded indicia 228A (FIG. 8) and/or printed indicia 228B (FIG. 7) on strap 216, to alert the surgeon as to the diameter of the button aperture 220. An extension arm 222 extends from button 218 on a side opposite the side with which strap 216 cooperates. A half-moon shaped enlargement 224 is formed at the one end of extension arm 222 to facilitate manipulation of extension arm 222 by a user. Adapter body 212 also includes a lip 226 to facilitate placement and removal of adapter seal 210 from a cannula housing 300 (see FIGS. 9A–9C, discussed below).

Adapter body 212 includes a transverse face 230 which is of reduced thickness in central region 232 surrounding aperture 214, thereby increasing the resilience and flexibility thereof and facilitating the introduction and removal of instrumentation in sealing engagement therewith. Adapter body 212 also includes lip projection 234 which is spaced from and surrounds central region 232. Lip projection 234 is adapted to contact stabilizer plate 236 which is preferably received by adapter body 212, as discussed below. The contact between lip projection 234 and stabilizer plate 236 forms a seal therebetween.

Adapter body 212 is of substantially rectangular configuration and includes rounded corners 238. The shape of body potion 212 corresponds to the shape of the Surgiport* cannula housing 300 which is marketed by United States Surgical Corporation, Norwalk, Conn. and shown in FIGS. 9A–9C hereto. An alignment notch (not pictured) and a trapezoidal projection 240 are formed in adapter body 212 to facilitate cooperation with corresponding structures on the Surgiport* cannula housing 300. As will be readily apparent to one of ordinary skill in the art, however, adapter body 212 may be fabricated in a variety of shapes and sizes to facilitate its use with other cannula assemblies, e.g., cannula assemblies marketed by other manufacturers, without departing from the teachings of the present invention.

Adapter body 212, including strap 216, button 218 and extension arm 222, is fabricated from an elastomeric material, e.g., santoprene or natural rubber, to provide a desired degree of resilience and flexibility thereto. This resilience and flexibility are desirable to allow efficient interaction between adapter seal 210 and cannula assembly 300, and to facilitate sealing engagement with an instrument passed through aperture 214. Moreover, the resilience and flexibility of strap 216 and button 218 facilitates the repositioning of button 218 relative to the body potion of adapter body 212 and the sealing engagement of button 218 with stabilizer plate 236, as discussed below. As will be apparent to one of ordinary skill, alternative materials may be selected for the fabrication of various components of the adapter seal 210 of the invention, keeping in mind the desired interaction between button 218 and body portion of adaptor body 212. Thus, although adapter body 212 is preferably of integral construction, portions of adapter body 218, e.g., the body portion, strap 216 and/or button 216, may be fabricated separately and joined to each other post-fabrication by known means.

The adapter seal of the present invention is further contemplated to include a plurality of straps associated with one or more side walls of the adapter body, each strap being associated with a button or like seal component having an aperture of a different size 321 (FIG. 6A). Thus, for example, an adapter body of the invention could include four straps, one extending from each side of a square or rectangular adapter body, the four straps cooperating with seal components having apertures of, for example, 5 mm, 7 mm, 10 mm and 12 mm. In this way, the surgeon would be allowed to selectively reduce the aperture of a cannula assembly to receive instruments of varying diameter. The multiple buttons/seal components are optimally designed to stack, i.e., the surgeon may nest a button having a 5 mm diameter aperture into a button having a 8 mm, thereby progressively reducing the diameter of the aperture of the seal adapter of the invention.

Adapter body 212 is adapted to receive stabilizer plate 236 which is made of substantially rigid material, e.g., an ABS polymer resin. Stabilizer plate 236 includes a substantially planar body member 237 and a proximally directed cylindrical projection 242 which defines a central orifice 244. The diameter of orifice 244 is selected to frictionally engage the outer surface 219 of button 218. Outer surface 219 of button 218 preferably includes an outwardly directed, arcuate geometry, as best seen in FIG. 8, to enhance the frictional engagement between button 218 and cylindrical projection 242 of stabilizer plate 236. Stabilizer plate 236 performs two principal functions in the adapter seal 210 of the present invention: first, stabilizer plate 236 improves the reliability of the seal provided by adapter seal 210 in conjunction with a surgical instrument inserted through aperture 214, as described in connection with stabilizer plate 28 and seal adapter 10 hereinabove; second, stabilizer plate 236 frictionally and sealingly engages button 218 when it is desired to reduce the effective aperture of seal adapter 210 by placing button aperture 220 in axial alignment with aperture 214. In this way, the surgeon may efficiently and efficaciously reduce the diameter of the cannula assembly to which adapter seal 210 is mounted.

As with stabilizer plate 28 discussed above, stabilizer plate 236 may be provided with a region of increased cross-section (not pictured) surrounding orifice 244 to enhance the ability of stabilizer plate 236 to maintain the seal between adapter body 212 and an instrument inserted therethrough. Stabilizer plate 236 is adapted to fit snugly within a peripheral notch 246 formed in adapter body 212. When fitted therewithin, planar body member 237 of stabilizer plate 236 lies in substantial parallel alignment with transverse face 230 of adapter body 212. A cutout 248 is provided along one edge of body member 237 to cooperate with alignment notch 250 of adapter body 212.

The body portion of adapter body 212 includes side walls 252 which define a peripheral rim thereof and an interior region 254. The body portion also includes interior walls 256 which, in conjunction with side walls 252, define a channel 258 which extends around the perimeter of the body portion. A pair of inwardly directed beads 260a and 260b and a lip 262 are formed on the interior face of side walls 252. Channel 258 is adapted to receive proximally extending faces 302 on cannula housing 300 (see FIGS. 9A–9C). Beads 260a, 260b and lip 262 provide increased frictional engagement between adapter seal 210 and cannula housing 300, thereby increasing the force required to separate one from the other.

Figure 9A:
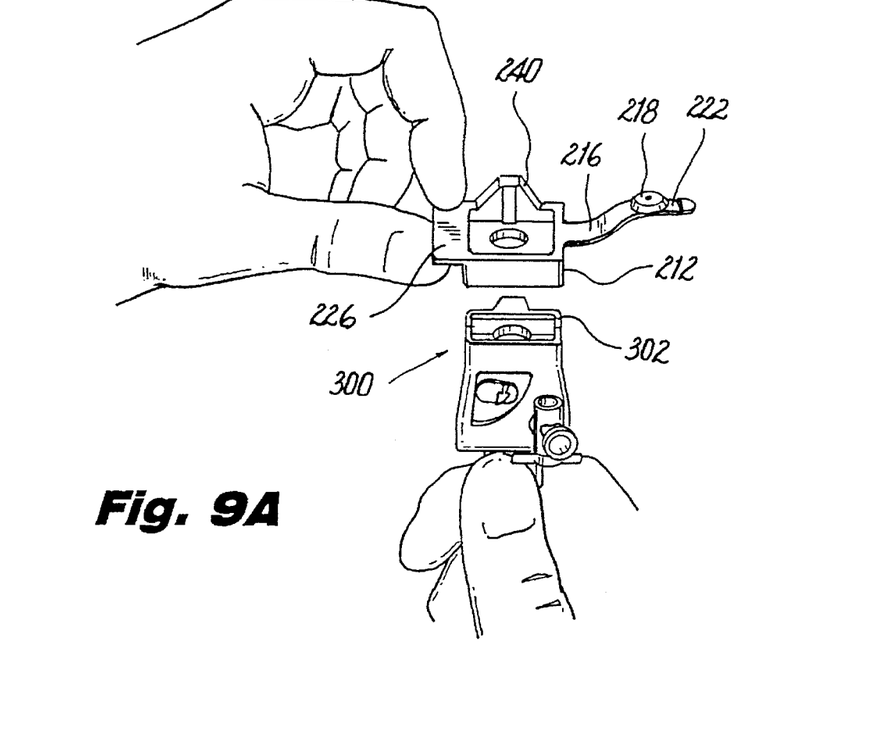
FIGS. 9A, 9B and 9C are schematic views of the alternate embodiment of the invention being mounted to and utilized in conjunction with a cannula housing.
Figure 9B:
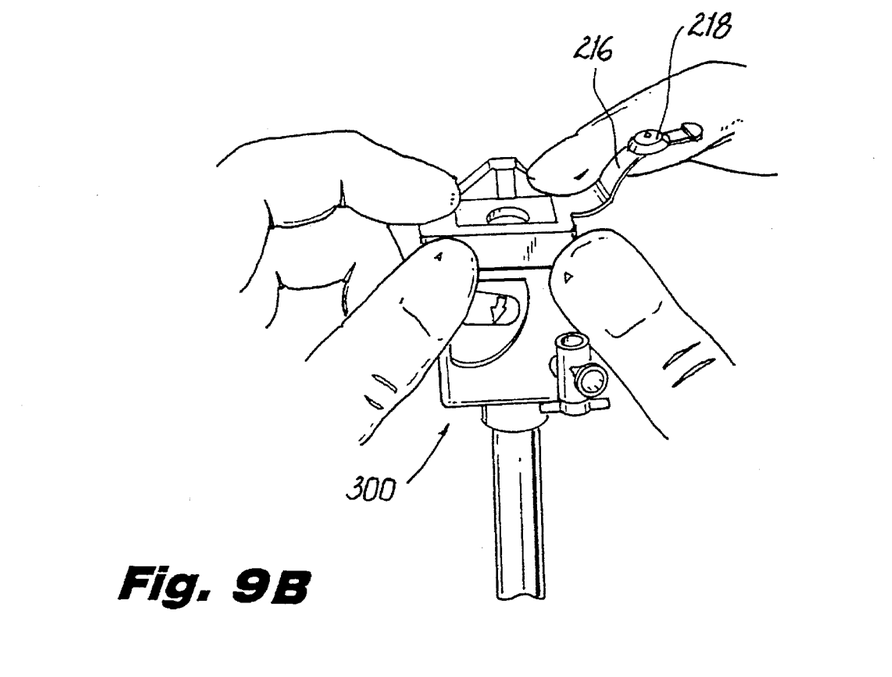

In use, a surgeon places a cannula assembly through a body wall in a conventional manner such that a port of entry for surgical instrumentation is provided. The surgeon may utilize instrumentation sized to cooperate with the selected cannula assembly, and particularly the seal assembly of the selected cannula assembly, without loss of pneumoperitoneum gas. If the surgeon desires to use instruments of smaller diameter than the cannula assembly's seal assembly is designed to accommodate, an adapter seal 210 of the present invention may be mounted to the cannula assembly as shown in FIGS. 9A and 9B. The surgeon aligns channel 258 with the proximal extending faces 302 on the cannula housing 300. Adapter seal 210 is firmly mounted on the cannula housing by pressing downward on adapter body 212 such that beads 260a, 260b and lip 262 engage the faces 302 of the cannula housing 300. A seal is thus formed between the cannula housing 300 and adapter seal 210.

Figure 9C:
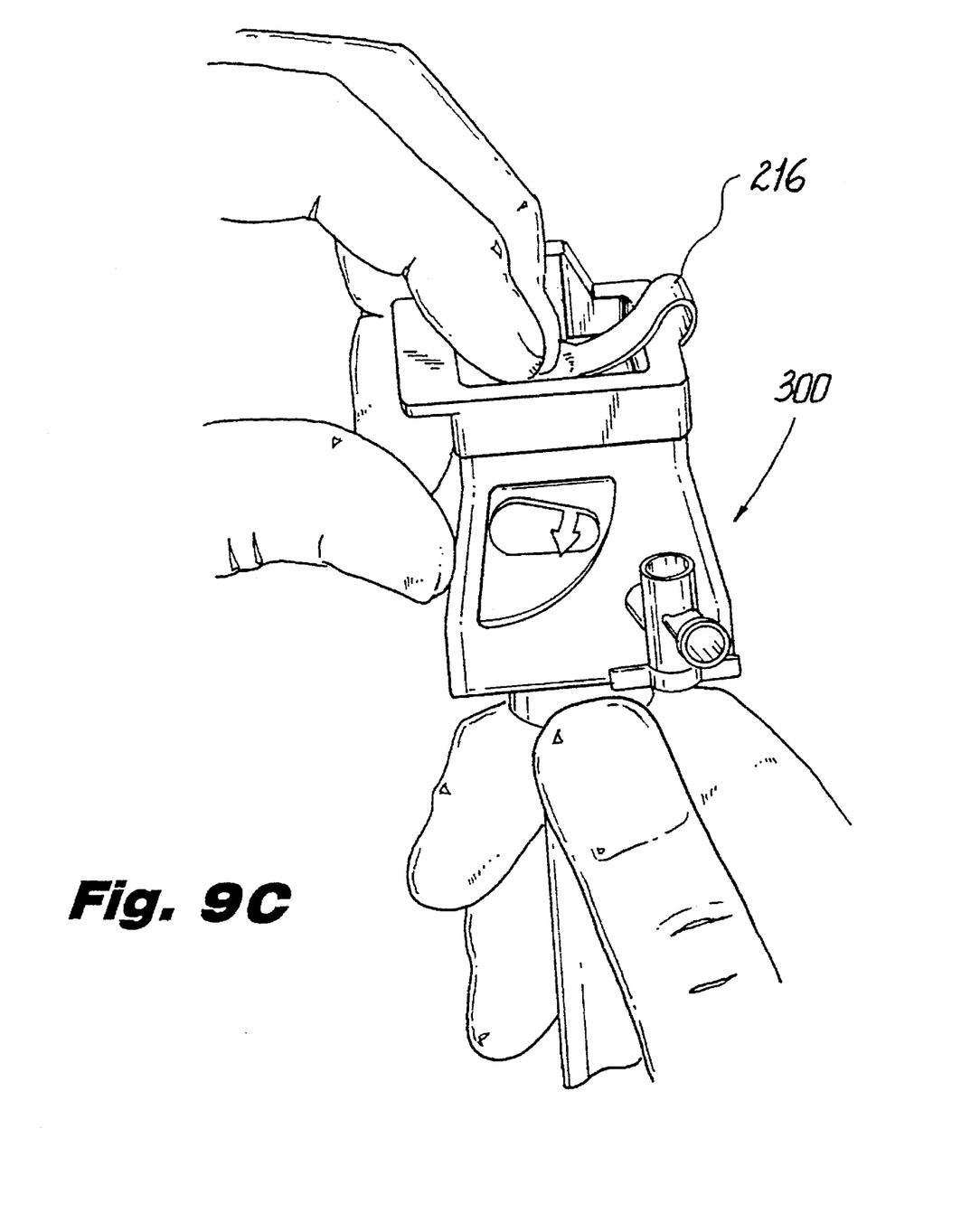

The surgeon proceeds with the surgical procedure by inserting surgical instrument(s) through aperture 214 in adapter body 212. Adapter body 212 thus sealingly engages the surgical instrument, thereby providing a gas seal therebetween. Stabilizer plate 236 restricts the freedom of movement of the instrument relative to the adapter seal 210, thereby ensuring a seal will be maintained between the instrument and adapter body 212. As the surgical procedure continues, if the surgeon desires to use a different sized instrument through cannula assembly 300, button 218 may be repositioned so that button aperture 220 is in alignment with aperture 214 in body member 212. As shown in FIGS. 9B and 9C, button 218 may be repositioned by flexing strap 216 so that button 218 effectively sweeps in an arcuate path relative to body member 212. Button 218 is brought into frictional engagement with stabilizer plate 236, thereby fixing the position of button 218 relative to body member 212 and providing a seal therebetween.

The surgeon is now free to use a smaller diameter instrument through button aperture 220. For example, in one embodiment of the invention, aperture 214 is on the order of 9.5 mm in diameter, thereby accommodating instruments ranging in diameter from 10 to 12 mm, and button aperture 220 is on the order of 4.5 mm in diameter, thereby accommodating instruments in the 5 mm diameter range. The adapter seal 210 of the invention thus allows the surgeon to utilize a variety of instruments, e.g., 5 mm instruments such as graspers, dissectors, electrocautery devices, scissors and the like, as well as 10 to 12 mm instruments such as clip appliers and endoscopic stapling devices, through a single cannula assembly in an efficient and efficacious manner.

At any point during the procedure, button 218 may be removed from engagement with body member 212 and left suspended by strap 216 from body member 212 while the procedure continues through aperture 214. Button 218 is always in ready position for repositioning in alignment with aperture 214, as discussed above, for repeated use of smaller diameter instrumentation. Alternatively, a different adapter seal 210 having a different size aperture 214 and/or button aperture 220 may be placed on the cannula housing 300, or the cannula assembly 300 may be utilized without an adapter seal 210, i.e., with only the seal assembly present in the cannula housing 300. In an embodiment of the invention which includes multiple straps, as described above, the surgeon may alternatively nest a second button having an aperture of reduced diameter into button 218, thereby reducing the effective diameter of the assembly.

Figure 10:
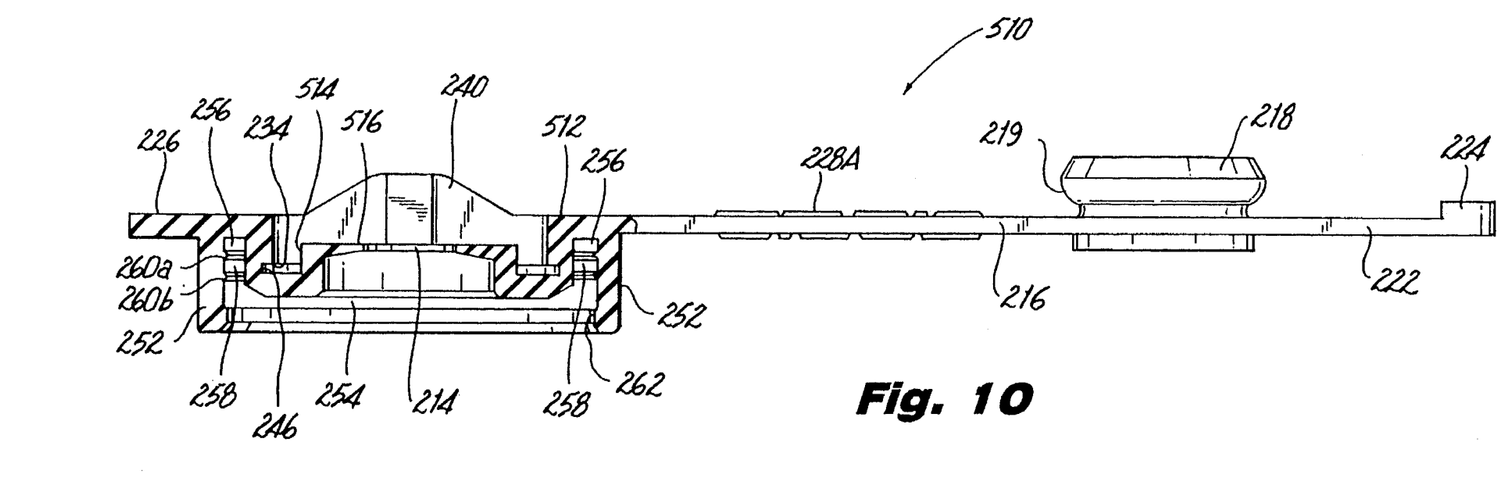
FIG. 10 is a side view, partially in cross-section, of a further alternate embodiment of the present invention.
Figure 11:
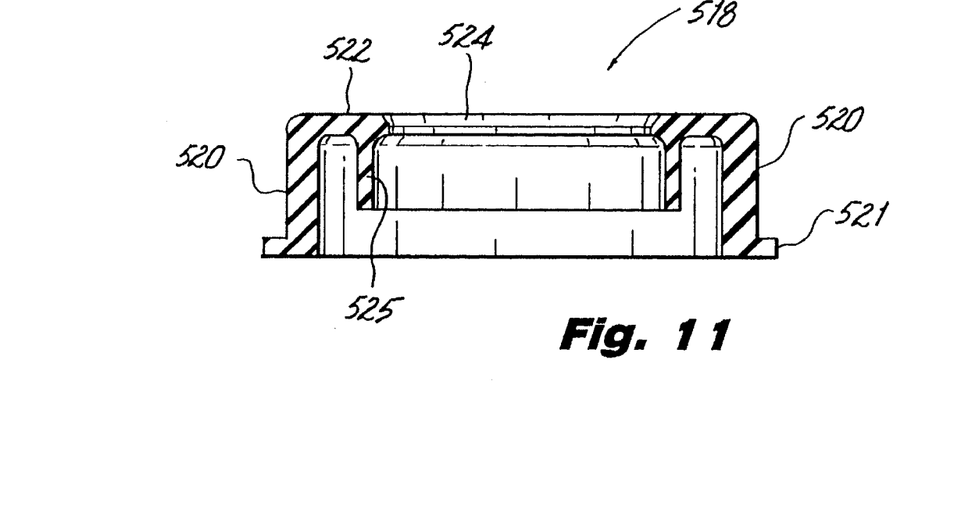
FIG. 11 is sectional side view of a stabilizer plate for use with the alternate embodiment of FIG. 10.

Turning to the alternate embodiment of FIGS. 10 and 11, adaptor seal 510 is very similar to adaptor seal 210 described hereinabove and like reference numerals are used to designate like structures. Focussing on the differences between the respective adaptor seals, adaptor body 512 of adaptor seal 510 includes inner, upstanding wall 514 which joins with transverse face 516. Aperture 214 is formed in transverse face 516. The elevated positioning of aperture 214, based on the height of upstanding wall 514, provides additional flexibility to adaptor body 512 and helps to maintain the perimeter of aperture 214 in sealing engagement with an instrument inserted therethrough. Stabilizer plate 518 includes upstanding wall 520, peripheral flange 521, transverse face 522 that includes a central orifice 524, and inner wall 525. Peripheral flange 521 is adapted to be received within peripheral notch 246 in adaptor body 512. Inner wall 525 provides additional guidance to an instrument inserted through central orifice 524, helping to maintain the alignment of the instrument with aperture 214 in adaptor body 512. Upstanding wall 520 serves to space transverse face 522 of stabilizer plate 518 from transverse face 516 of adaptor body 512. This spacing allows stabilizer plate 518 to more effectively ensure that a seal is maintained between agressively manipulated instruments and the perimeter of aperture 214.

Although the illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention. For example, the straps described hereinabove may be replaced by hinge assemblies to facilitate placement of a reduced diameter aperture in alignment with the cannula seal assembly. As with the straps described above, the hinge assemblies would allow the button to remain suspended from the adapter seal body while the procedure continued through the cannula assembly aperture. Other changes and modifications would be equally apparent to one of ordinary skill in the art from the detailed description contained herein.

We claim:

1. An adapter seal for use with a cannula assembly, comprising:

(a) an adapter body member which includes a body member aperture of a first diameter;

(b) a stabilizer plate operatively associated with said adapter body member and including a stabilizing aperture formed therethrough;

(c) a button having a button aperture of a second diameter, said second diameter being less than said first diameter; and (d) at least one additional button having an additional button aperture of a third diameter, said third diameter being less than said first and second diameters, wherein each of said buttons is joined to said adapter body member such that each of said buttons may be selectively positioned relative to said body member by individually inserting each of said buttons at least partially through said stabilizing aperture, said stabilizer plate frictionally engaging each of said buttons, with each of said button apertures in alignment with said body member aperture when inserted at least partially through said stabilizing aperture.

2. The adapter seal of claim 1, wherein said button is joined to said adapter body by a member selected from the group consisting of a strap and a hinge.

3. The adapter seal of claim 2, wherein said button is joined to said adapter body by a strap and said strap is fabricated from an elastomeric material.

* * * * *